(12) United States Patent
Oding

(10) Patent No.: US 10,605,709 B2
(45) Date of Patent: Mar. 31, 2020

(54) MOUNTING MEDIUM FOR EMBEDDING A SAMPLE MATERIAL AND A METHOD OF MOUNTING A SAMPLE MATERIAL IN A MOUNTING MEDIUM

(71) Applicant: Struers ApS, Ballerup (DK)

(72) Inventor: Per Buus Oding, Fredensborg (DK)

(73) Assignee: STRUERS APS, Ballerup (DK)

( * ) Notice: Subject to any disclaimer, the term of this patent is extended or adjusted under 35 U.S.C. 154(b) by 161 days.

(21) Appl. No.: 15/563,434

(22) PCT Filed: Mar. 29, 2016

(86) PCT No.: PCT/EP2016/056762
§ 371 (c)(1),
(2) Date: Sep. 29, 2017

(87) PCT Pub. No.: WO2016/156288
PCT Pub. Date: Oct. 6, 2016

(65) Prior Publication Data
US 2018/0088011 A1    Mar. 29, 2018

(30) Foreign Application Priority Data
Mar. 31, 2015  (DK) ................................. 2015 70190

(51) Int. Cl.
*C08K 3/08*    (2006.01)
*G01N 1/36*    (2006.01)
(Continued)

(52) U.S. Cl.
CPC ................. *G01N 1/36* (2013.01); *B22F 3/16* (2013.01); *B22F 7/02* (2013.01); *C08K 3/08* (2013.01);
(Continued)

(58) Field of Classification Search
CPC ...... G01N 1/36; G01N 2001/364; B22F 3/16; B22F 7/02; B22F 2301/52; B22F 2304/10;
(Continued)

(56) References Cited

U.S. PATENT DOCUMENTS 3,268,644 A * 8/1966 Cain, Jr. .................. G01N 1/32
264/266
2004/0022358 A1* 2/2004 Tomita ..................... C08K 3/08
378/70
(Continued)

FOREIGN PATENT DOCUMENTS

| CN | 102504485 A | 6/2012 |
|---|---|---|
| JP | S5670445 A | 6/1981 |
| WO | 2011039469 A1 | 4/2011 |

OTHER PUBLICATIONS

International Preliminary Report on Patentability issued in corresponding International Application No. PCT/EP2016/056762, dated Jun. 13, 2017, 7 pages.
(Continued)

*Primary Examiner* — David J Bolduc
(74) *Attorney, Agent, or Firm* — Snyder, Clark, Lesch & Chung, LLP

(57) ABSTRACT

A method of embedding a sample material in a mounting medium with reduced cycle times and a mounting medium for embedding a sample material.
The method includes the steps of:
preparing a granular mounting medium by blending a granular resin and a granular filler,
placing a sample material and said granular mounting medium in a moulding cavity,
followed by the steps of:
heating, for a first period of time, said moulding cavity including said granular mounting medium thereby producing a sintering mounting medium,
(Continued)

cooling, for a second period of time, said moulding cavity including said mounting medium thereby producing a solid mounting medium embedding said sample material.

21 Claims, 4 Drawing Sheets

(51) Int. Cl.
  *B22F 3/16*   (2006.01)
  *B22F 7/02*   (2006.01)
  *C09K 5/14*   (2006.01)
  *C22C 1/05*   (2006.01)
  *B22F 3/10*   (2006.01)

(52) U.S. Cl.
  CPC ........ *C09K 5/14* (2013.01); *B22F 2003/1042* (2013.01); *B22F 2301/052* (2013.01); *B22F 2304/10* (2013.01); *B22F 2998/10* (2013.01); *B22F 2999/00* (2013.01); *C08K 2003/0812* (2013.01); *C08K 2201/001* (2013.01); *C08K 2201/005* (2013.01); *C22C 1/05* (2013.01); *G01N 2001/364* (2013.01)

(58) Field of Classification Search
  CPC ........ C08K 3/08; C08K 2201/01; C08K 3/05; C08K 2001/0812; C09K 5/14
  See application file for complete search history.

(56) References Cited

U.S. PATENT DOCUMENTS

| | | | |
|---|---|---|---|
| 2009/0155608 A1* | 6/2009 | Nomura | C09J 9/02 428/457 |
| 2010/0300053 A1* | 12/2010 | Alary | C04B 35/185 55/523 |
| 2013/0113121 A1* | 5/2013 | Okada | H01L 23/295 257/787 |
| 2013/0295280 A1 | 7/2013 | Fournee et al. | |
| 2016/0340191 A1* | 11/2016 | Ikemiya | C01B 21/0648 |
| 2017/0074755 A1* | 3/2017 | Adiga | G01N 1/06 |

OTHER PUBLICATIONS

Bjerregaard, Leila et al. "Metalog Guide: Your Guide to the Perfect Materialographic Structure," Struers A/S, Dec. 31, 2002, retrieved from <https://www.struers.com/-/media/Library/Brochures/English/Metalog-Guide.pdf?dmc=1&ts=20180420T0754064758>, 115 pages.

* cited by examiner

MOUNTING MEDIUM FOR EMBEDDING A SAMPLE MATERIAL AND A METHOD OF MOUNTING A SAMPLE MATERIAL IN A MOUNTING MEDIUM

The present invention relates, according to a first aspect, to a granular mounting medium for embedding or mounting a sample material.

According to a second aspect, the present invention relates to a method of mounting a sample material in a mounting medium.

According to a third aspect, the present invention relates to a method of preparing a granular mounting medium for embedding or mounting a sample material.

A granular material typically is a conglomeration of discrete solid particles. Powders are a special class of granular materials due to their small particle size. Hence, the expression "granular", in the context of the present disclosure, also refers to powders as such.

The term "metallic" throughout this specification refers to a material having metal like character and properties which are associated with the elements classified as metals in the periodic table.

The term "sintering" throughout this specification refers to a process of compacting and forming a solid mass from a granular material by applying heat and/or pressure without melting it to the point of liquefaction. Sintering typically cause a powdered material to become a monolithic bulk material by diffusion between individual powder/granular particles.

The present specification refers to "particle size". Throughout this specification, particle size may refer to particle size distribution D50 which is also known as the median diameter or the medium value of the particle size distribution; it therefore is the value of the particle diameter at 50% in the cumulative distribution. For example, if D50=60 µm, then 50% of the particles in the sample are larger than 60 µm, and 50% smaller than 60 µm.

BACKGROUND

Preparing sample materials such as materialographic and/or metallographic samples for analysis such as for microscopy or SEM for hardness testing or image analysis, is a challenging and often time consuming task; inter alia as each sample must be fixed by moulding in an often modular sample holder in order to facilitate not only the analysis, but also the preparation of the sample material for the analysis.

Preparation for analysis includes various steps of cutting and polishing the sample material in order to present a perfect surface of the sample material.

In order to fix a sample material in a sample holder, the sample material typically is embedded in a mounting medium prior to preparation and subsequent analysis. By this, protection as well as easy handling of the often small and fragile samples are obtained.

The availability of sophisticated sample material embedding systems and/or sample mounting systems has made the process of embedding the samples easier. The sample mounting process is, despite the sophisticated techniques, still a time consuming operation; especially since cycle times required by any steps of heating and/or cooling are limited significantly by the mounting medium's ability to transfer heat into and out from the embedding matrix. The obvious solution for decreasing the cycle times required by heating and/or cooling would be to apply either very high or very low temperatures in order to heat or cool the mounting medium and thereby expedite the mounting/sintering process. This, however, is undesirable inter alia as:
large temperature gradients in effect compromise the integrity of the mounting medium, and
large temperature gradients cause the mounting media to sinter with a less than an adequate or suitable rate to give a homogeneous sintering of the matrix within short cycle times.

Typically, the sample material preparation process includes following steps:
sectioning the sample into one or more suitable sections,
mounting the sectioned sample material in a mounting medium to facilitate handling and to protect the sample material,
grinding the mounted sample, and
polishing the mounted sample.

The embedding material, or mounting medium, must be composed or chosen such that the mounting medium offers satisfactory properties with respect to fixation and edge retention of the sample material within the mounting medium.

Typically, the sample material is embedded in the mounting medium by means of a sintering process taking place in a compression mould. Heat may be applied to the mould to facilitate the mounting process. Furthermore, the mould may be actively cooled in order to facilitate cooling of the mould including the mounting medium and sample material—thereby reducing the cycle times required by heating and/or cooling.

The speed or rate at which the mould including mounting medium and sample material may be heated correlates to the cycle time of a moulding process and vice versa. Likewise applies in case the mould is actively cooled in a following step.

One object of the present invention is to set forth a mounting medium configured for reducing the cycle time(s) of the mounting process.

Moreover, it is an object of the present invention to set forth a method of mounting sample materials. The method is configured for reducing the cycle time(s) of the mounting process without compromising the integrity of the mounting medium including the integrity of contact faces between the mounting medium and the sample material. Furthermore, the method is configured for preventing damage to the sample material due to chemical in compatibility and or preventing interfering with Energy-Dispersive X-ray spectroscopy spectra of typical metallographic sample materials, e.g. stainless steel.

Finally, it is an object of the present invention to set forth a mounting medium, and a method of producing a mounting medium, configured for lessening temperature gradients throughout the mounting medium during heating and/or cooling.

U.S. Pat. No. 3,268,644 A discloses a method of making an assembly including a specimen holder and a specimen for the purpose of subjecting the specimen to etching by means of an electric discharge. The object of the invention according to U.S. Pat. No. 3,268,644 A is to provide a method of making a specimen assembly which exposes only a small part of the surface of the specimen to an electric discharge and to provide effective means for impressing an electrical potential to the embedded specimen. The method includes placing the specimen in a block of mouldable electrically conducting material consisting of a mixture of two parts phenolic condensation powder (Bakelite) with a mica filler and/or wood flour filler or the like and one part aluminium filler. This recipe thus results in a powder having 66.6% non-metal and 33.3% metal. According to the reference, the said non-metal/metal ratio allows for electrical potential to be impressed between the specimen and an anode. The mixture according to U.S. Pat. No. 3,268,644 A is chemically cured under a heat-treatment process. The reference provides no teaching with respect to any of:

limiting gaps between the hardened/cured powder and the specimen,
the heat conductivity of the said hardened powder,
the workability of the hardened powder,
hardening by means of a sintering process,
chemical compatibility with the sample during subsequent materialographic and/or metallographic preparation steps, or
avoid interference with Energy-dispersive X-ray spectroscopy spectra of typical metallographic samples.

JP 5026794 A discloses a non-metallic resin for embedding sample materials prior to preparation and analysis.

US 2004 028563 A discloses a tool for making a mounting or holder for a tablet-shaped sample material which is to undergo analysis in/by an analytical instrument.

Moreover, today there are hot mounting resins available configured for applications suitable for electrolytic polishing. One hot mounting media includes acrylic resin, iron powder and graphite filler. This mounting media is marketed under the name ConduFast and is composed of 30-60 W % acryl, 30-60 W % iron and 5-15 W % graphite.

BRIEF DESCRIPTION OF THE INVENTION

The present invention seeks in general to reduce cycle times of hot mounting processes for sample materials. Moreover, the present invention seeks to set forth a granular mounting medium which allows for a reduction in cycle times of hot mounting processes while also being cost-effective and easy to produce.

In accordance with the first aspect of the present invention, the cycle times are reduced significantly by means of the granular mounting medium as per the introductory part of this specification wherein the granular mounting medium includes a mixture of a granular resin and a granular metal filler. The metal filler may constitute granular aluminium. The weight ratio between the granular resin and the granular metal filler may be in the range of 20-40% granular resin and 60-80% granular metal filler. Alternatively the ratio may be in the range of 28-32% granular resin and 68-72% granular metal filler or 30% granular resin and 70% granular metal filler.

Tests has shown that the cycle times, i.e. heating and cooling, may be lowered from about 5 minutes to about 3½ minutes without imposing significant temperature gradients to or throughout the mounting medium.

The mounting medium according to the first aspect of the present invention is configured, or composed, such that the mounting medium allows for lowering the heat transfer gradients. This will result in increased thermal energy transfer, or increased heat conductivity, between the walls of the mould and the mounting.

Increased heat conductivity of the mounting medium reduces the time required for mounting the sample material as the time required for uniformly heating the batch to a certain temperature is reduced significantly.

In accordance with the second aspect of the present invention, the cycle times are reduced significantly by means of the method of mounting a sample material as per the introductory part of this specification wherein the method includes the steps of:

placing a sample material and a granular mounting medium comprising a granular resin and a granular metal filler in a moulding cavity,
heating, for a first period of time, said moulding cavity including said granular mounting medium thereby producing a sintering mounting medium,
cooling, for a second period of time, said moulding cavity including said mounting medium thereby producing a solid mounting medium embedding said sample material.

According to one embodiment, the granular mounting medium, or the acrylic resin in the granular mounting medium, may be configured for fixating the sample material by means of sintering. By this, a chemically non-reactive mounting medium is provided requiring only few safety measures for handling, storage and disposal etc.

According to one embodiment, the granular resin may have a particle size of 50-100 µm, alternatively 75-95 µm, alternatively 50 µm. The particles may be spherical.

According to one embodiment, the granular metal filler may have a particle size of about half the particle size of the granular resin According to one embodiment, at least 95% of the granular metal filler may have a particle size of less, or substantially less, than 200 µm and maximum 5% of the granular metal filler may have a particle size in excess of 200 µm.

According to one embodiment, the metal filler particles may be elongate and/or filigree-like and/or constitute flakes.

According to one embodiment, the largest granular metal filler particles may have a length of 200 µm and the majority of the granular metal filler particles may have a length below 10 µm.

The above embodiments inter alia are set forth to counter inhomogeneous blends, and thereby segregation, of the mounting medium.

According to one embodiment, the first period of time, for heating the mounting medium, and the second period of time, for cooling the mounting medium, is determined inter alia by the ratio between the granular resin and the granular metal filler.

According to one embodiment, the first period of time and the second period of time are determined inter alia by the thermal conductivity of the mounting medium. The thermal conductivity in effect is determined by the ratio between the granular resin and the granular metal filler and the metal chosen as the metal filler.

According to one embodiment, the method may be or form part of a series production of sample preparations where the cycle time of each production is determined by means of controlling heat conductivity of the mounting medium.

According to one embodiment, the heat conductivity may be controlled by means of blending a granular resin with granular metal filler having heat conductivity which is higher than the heat conductivity of the granular resin.

According to one embodiment, the granular metal filler may be aluminium. By this, the following inter alia is achieved:

optimum heat conductivity of the mounting medium and thereby relatively small temperature gradients during heating and/or cooling of the mounting medium. The extraordinary high heat conductivity is obtained as aluminium particles, during moulding/sintering, compile around the granular resin and thereby form internal bridges within the moulded mounting media. In the abovementioned mounting media named ConduFast, where the metal filler is iron, the metal particles tend not to compile around the resin and, consequently, i.e. no internal metal bridges within the moulded mounting media are formed. The graphite in ConduFast forms around the acrylic particles thereby establishing electrical connection through the mounting medium via the iron particles, electrical conveyance to the sample material through the mounting medium, density corresponding to the density of the resin which inter alia may constitute acryl or plastic. Corresponding densities to prevent segregation of the blend and facilitates formation of internal bridges, electrochemical and/or galvanic compatibility with the embedded samples, and a granular mounting medium made up from a blend of only two ingredients.

According to one embodiment, the granular resin may be acryl or equivalent material. The granular resin may as an alternative constitute a thermoplastic or thermosetting material.

The mounting medium may be provided as "ready to use" composition, possible packed in dosing containers and labelled accordingly. Alternatively, the mounting medium according to the present invention may be mixed or blended at the site of application, or even in the mould, to suit specific needs with respect to the thermal conductivity.

According to one embodiment, the step of placing the sample material and the granular mounting medium comprising a granular resin and a granular metal filler in a moulding cavity may be followed by a further step of placing a second metallic or non-metallic mounting medium in the moulding cavity such that the metallic mounting medium according to the first aspect of the present invention serves as a backing for the second mounting medium. By this, higher thermal conveyance is rendered to the mount even in case the second mounting medium is embodied as a mounting medium having relatively low thermal conveyance.

DETAILED DESCRIPTION

The present invention will in the below be explained in more detail with reference to the schematic FIGS. 1, 2 and 3.

Figure 1:
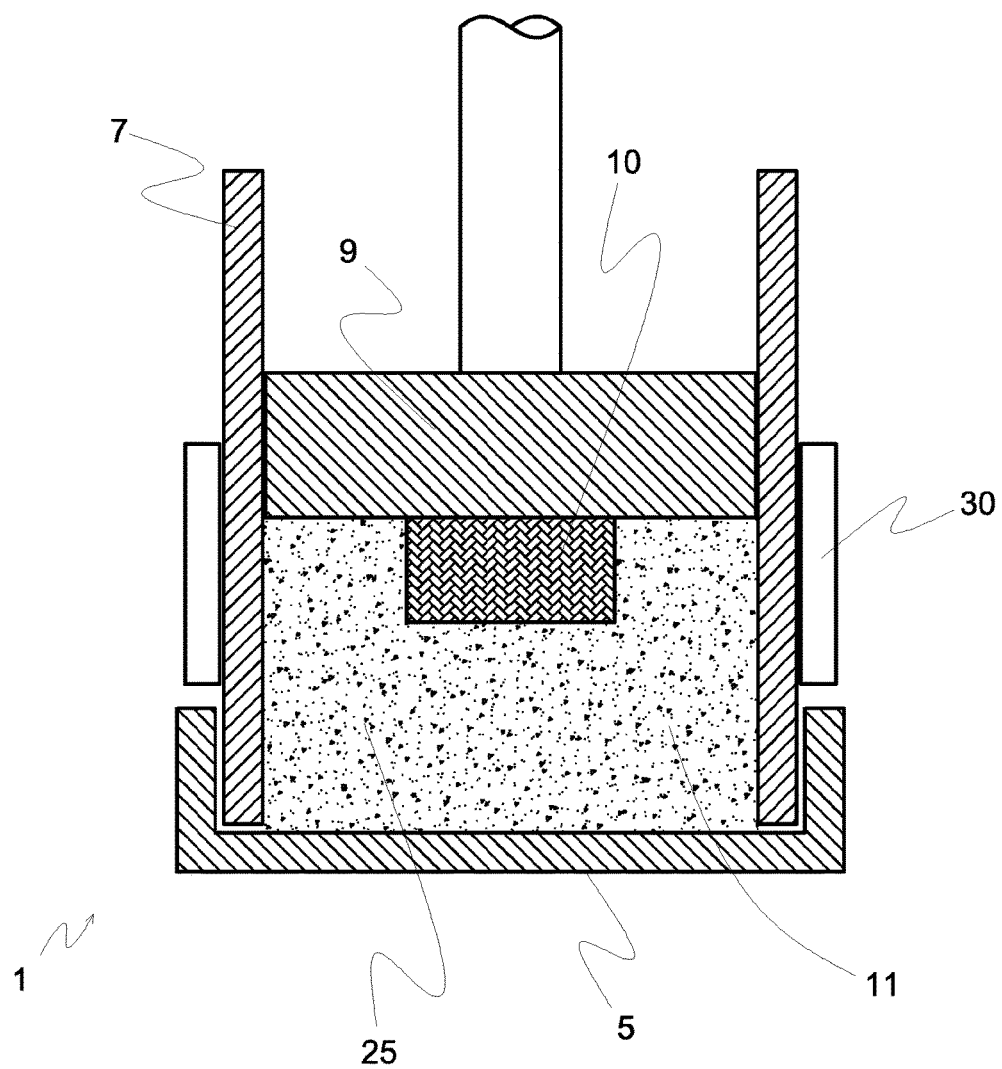
FIG. 1 shows, schematically, a sample material arranged in a compression mould.
Figure 3:
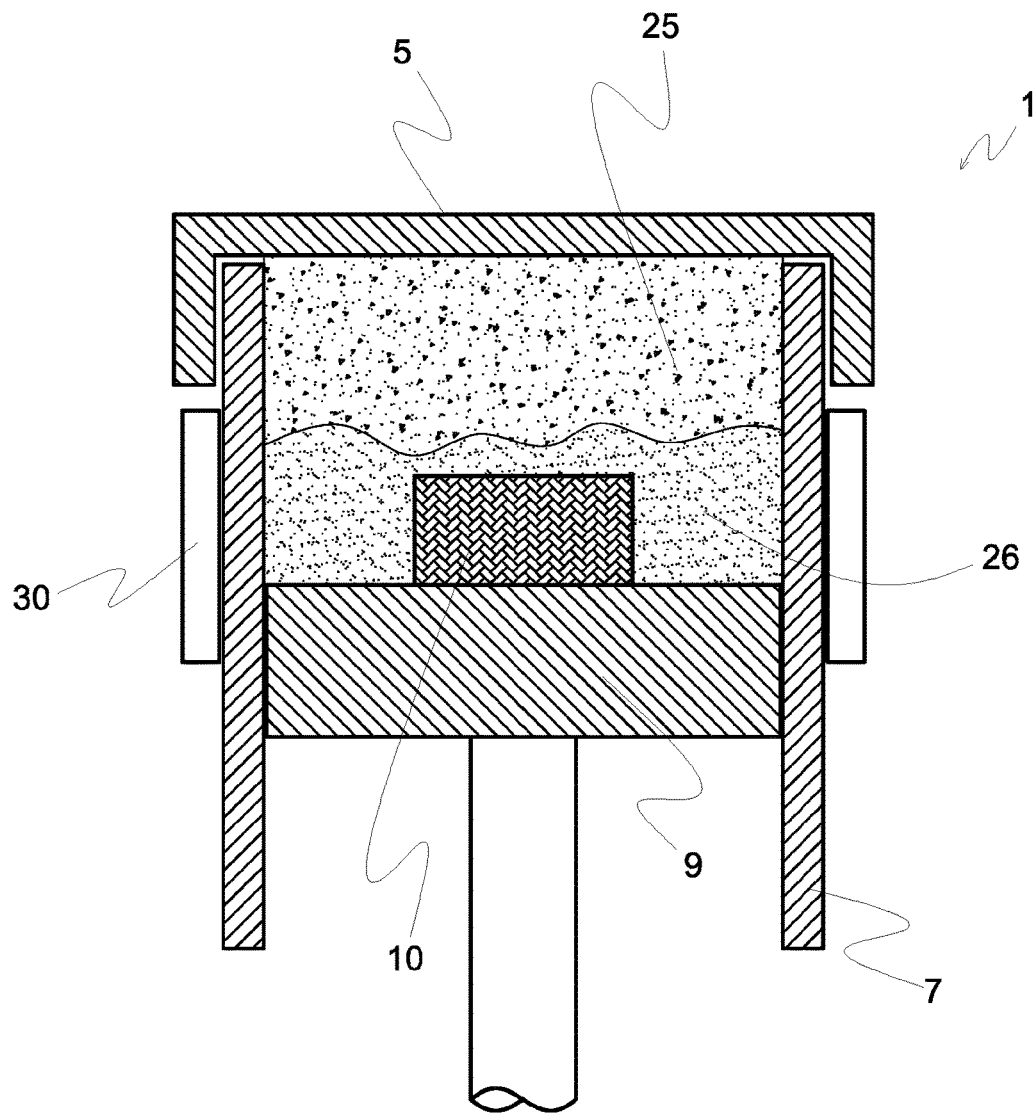
FIG. 3 shows, schematically, a sample material arranged in two different mounting media and arranged in a compression mould.

FIGS. 1 and 3 show a compression mould 1 including a lid or cover 5, walls 7 which may be embodied as a cylinder, and pressing means 9. The pressing means 9 may, as shown, be embodied as a ram.

The walls 7, the lid 5 and the pressing means 9 together define a cavity 11 configured for receiving a sample material 10 and the mounting medium 25, 26 in accordance the present invention.

Temperature regulating means 30, i.e. heating and/or cooling means 30, is in the depicted embodiments according to FIGS. 1 and 3 shown as means encircling the walls 7 or the compression mould 1.

In the embodiment according to FIG. 1, a mounting medium 25 is filled in the cavity 11 and a sample material 10 is arranged inside the cavity 11 and in the mounting medium 25 such that an upper face of the sample material 10 is in level with the upper face of the mounting medium 25 and, ultimately, the pressing means 9.

In the embodiment according to FIG. 3, which is upside-down the embodiment according to FIG. 1, the sample material 10 initially is placed on the pressing means 9 inside the cavity 11. As shown, a second mounting medium 26 may be filled in the cavity 11; possibly to cover the exposed faces of the sample material 10 resting on the pressing means 9. The second mounting medium 26 may be chosen in accordance with any desired properties or frames of costs etc. for the mounting medium 26. The first mounting medium 25 in accordance with the first aspect of the present invention may, as shown, be applied as a backing.

In the embodiment according to FIG. 3, the mounting medium may constitute the first mounting medium 25 only.

The cover or lid 5 may be connected to the walls of the mould 1 by means of not shown threads or equivalent.

The present invention is not in any way limited to a particular embodiment or type of mould; other types of mounting devices including some alternative kind of moulding cavity, or compression moulding cavity, may equally be applied without departing from the scope of the present invention.

As can be seen in FIG. 1, the mounting medium 25 constitutes a relatively homogeneous blend; this is secured inter alia by means of a number of embodiments according to the appended claims.

Tests have shown that the ratio between the density of the granular resin and the density of the granular filler preferably should be kept within a certain range in order to secure a homogeneous blend of granules. In case the blend is not homogeneous, strength properties, mounting gap between sample and mounting medium, and thermal properties of the mounting medium may be compromised.

The ideal filler, metallic or not, may be chosen to have the following properties:

The thermal conductivity of the filler should be as high as possible in order to get as high heat conductance during the mounting process as possible, The density of the filler should be as close as possible to the density of the resin granules in order to avoid segregation or sedimentation of the granule-filler mixture, In case electrical conveyance of the embedding medium is desired, a filler having suitable electrical properties may be chosen, Galvanic decomposition of the mounted sample should be avoided. This requires the filler to be galvanic inert. Alternatively, the filler material should be the sacrificial anode when combined with the typical metallic samples such as different steel types, and The filler should be acceptable with regards to safety and environmental impact, Aluminium filler, or aluminium based filler, fulfils the above criteria and is therefore in most embodiments preferable compared to other metals or inorganic compounds.

Specifically, noble metals with higher thermal conductivity (gold, silver, copper) are not suitable due to galvanic decomposition of typical samples such as steel and due to their higher density. The formation of oxide membrane on aluminium is, on the other hand, beneficial as the metal may be rendered passive as a result of the membrane.

Furthermore, aluminium has the benefit of being compatible with scanning electron microscopy (SEM) and Scanning electron microscopy with energy dispersive X-ray spectroscopy (SEM/EDX), which is frequently used with materialographic and/or metallographic samples.

Figure 2:
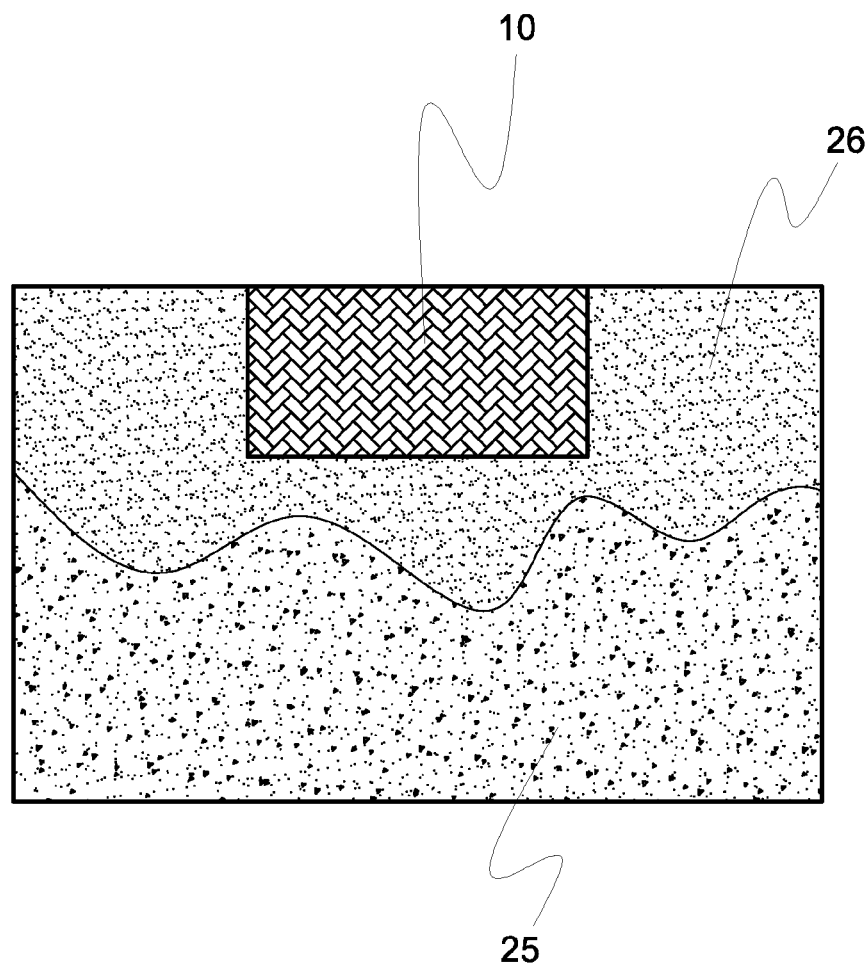
FIG. 2 shows, schematically, a sample material arranged in two different mounting media.

FIG. 2 shows, schematically, an embodiment of the present invention wherein a sample material 10 is arranged in two different mounting media; a first backing mounting medium 25 according to the present invention and a second mounting medium 26. The second mounting medium 26 may be chosen in accordance with any desired properties or frames of costs for the mounting medium 26. The embodiment is particular beneficial in case the mounting medium 25 according to the present invention is undesirable as the sole mounting medium, e.g. in case the granular metal filler is too soft compared to the sample material 10 leading to rounding of the sample edges during the subsequent preparation steps. Moreover, in case the filer according to the present invention disturbs the process of preparing the sample 10 for examination, it may be desirable to apply the embodiment according to FIG. 2.

Tests have shown that cycle times of samples 10 prepared in accordance with the embodiment as illustrated by FIG. 2 are significantly reduced.

When the sample is properly mounted in the mounting medium, the sample is ready for mechanical preparation and subsequent microscopic analysis or equivalent.

Figure 4:
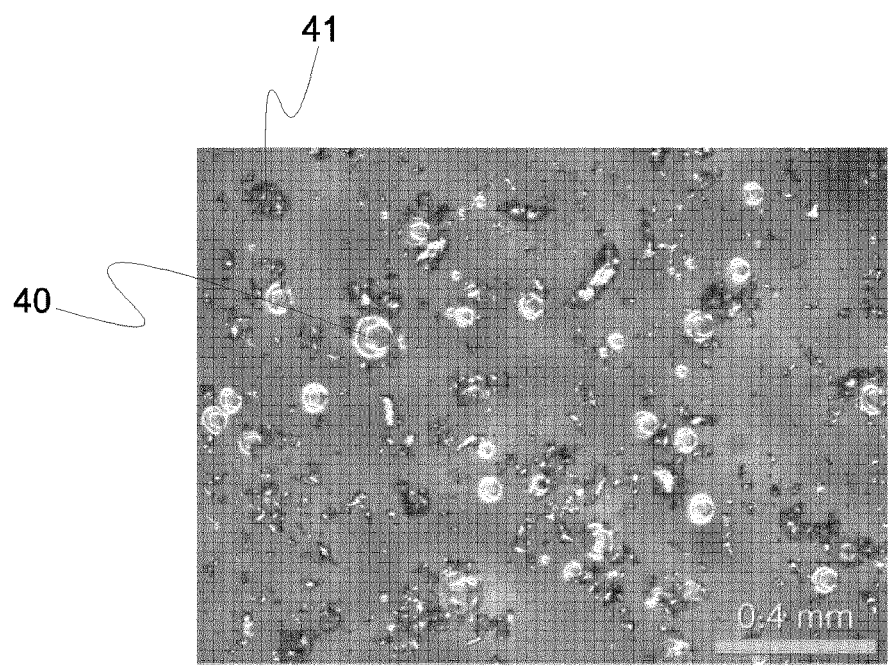
FIG. 4 shows an enlarged view of the granular mounting medium prior to moulding.

FIG. 4 shows an enlarged view of the granular mounting medium in its unsettled state, i.e. prior to moulding. The essentially round white circles 40 constitute acrylic particles and the smaller and darker particles 41 constitute aluminium particles. As can be seen, the size distribution of the aluminium particles 41 range from about the size of the acrylic particles 40 to significantly less. As can be seen, some of the particles approach 200 microns; however most of the aluminium particles 41 are much smaller.

Further, as can be seen in FIG. 4, the acrylic particles 40 are essentially uniform in size having a typical particle size of about 50 microns.

Figure 5:
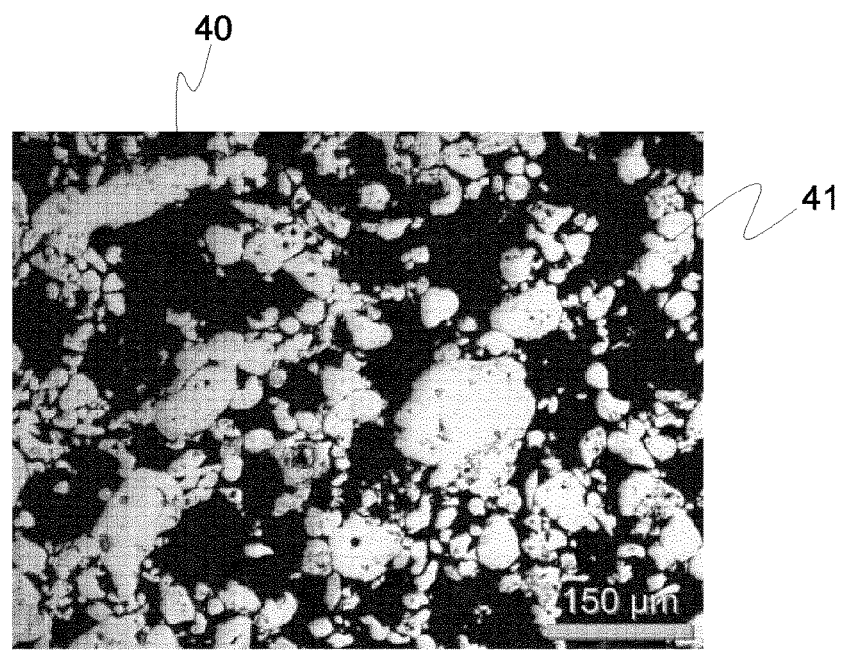
FIG. 5 shows an enlarged view of the mounting medium after moulding.

FIG. 5 shows an enlarged view of the moulded and thereby settled mounting media. In this view, the aluminium particles 41 is white and the settled acrylic resin black. As can be seen, the aluminium particles 41 has settled around the deformed acrylic particles 40.

The aluminium particles 41 provides, as can be seen in FIG. 5, and due to their ability to settle around the deformed acrylic particles 40, not only electrical conductivity by covering "surfaces" of acrylic particles, but also thermal conductivity—thereby creating a conductive path through the mounting medium without filling up the medium.

The mechanical preparation of the sample materials may, as mentioned in the introductory part of this specification, involve preparation by means of using abrasive particles in successively finer steps to strip material from the surface until achieving the desired result.

The present invention is not in any way limited to one or more of the illustrated embodiments. Features of one embodiment may be combined with, or replaced by, features of another, possibly not shown, embodiment without departing from the scope of the present invention.

The invention claimed is:

1. A granular mounting medium for a sample material, wherein said granular mounting medium is configured for fixating said sample material by means of a sintering process in a compression mould, said granular mounting medium (25) comprising:
    a chemically non-reactive mounting medium consisting of a mixture of a thermoplastic granular resin; and
    a granular metal filler,
    wherein the weight ratio between said granular resin and said granular metal filler is 20-40% granular resin and 60-80% granular metal filler, alternatively, 28-32% granular resin and 68-72% granular metal filler, alternatively 30% granular resin and 70% granular metal filler.

2. The granular mounting medium according to claim 1, wherein said granular mounting medium is configured for at least partially embedding and fixating a sample material.

3. The granular mounting medium according to claim 1, wherein at least 95% of said granular metal filler particles have a particle size below 200 µm and maximum 5% of said granular metal filler particles have a particle size in excess of 200 µm.

4. The granular mounting medium according to claim 1, wherein said granular metal filler particles constitute filigree particles having a typical particle size which is less than the particle size of said granular resin.

5. The granular mounting medium according to claim 1, wherein said granular metal filler is aluminium.

6. A sample material embedded in the granular mounting medium of claim 1.

7. A sample material embedded in two or more layers of mounting medium wherein a first layer of mounting medium constitutes the granular mounting medium of claim 1 and wherein a second layer of mounting medium constitutes a preferably non-metallic mounting medium.

8. The sample material according to claim 7, wherein said first layer is a backing layer for said second layer and wherein said second layer is fixating said sample material.

9. A method of mounting a sample material in a mounting medium, comprising:
    placing a sample material and said granular mounting medium of claim 1 in a moulding cavity,
    heating, for a first period of time, said moulding cavity including said granular mounting medium thereby producing a sintering mounting medium,
    cooling, for a second period of time, said moulding cavity including said mounting medium thereby producing a solid mounting medium embedding said sample material.

10. The method according to claim 9, wherein placing the sample material and the granular mounting medium of claim 1 in the moulding cavity is followed by placing a second preferably non-metallic mounting medium in the moulding cavity such that the metallic mounting medium serves as a backing for the second mounting medium.

11. The method according to claim 9, wherein placing the sample material and the granular mounting medium of claim 1 in a moulding cavity includes, in a sequential order:
    placing the sample material in the moulding cavity,
    filling a second preferably non-metallic mounting medium into the moulding cavity to at least partially cover or shroud the sample material, and
    filling the granular mounting medium consisting of said granular resin and said granular metal filler into the moulding cavity such that the metallic mounting medium serves as a backing for the second mounting medium.

12. The method according to claim 9, further comprising preparing the granular mounting medium by blending said granular resin and said granular metal filler.

13. The method according to claim 9, wherein said first period of time and said second period of time is determined based on the weight ratio between said granular resin and said granular metal filler.

14. The method according to claim 9, wherein said first period of time and said second period of time is determined based on a thermal conductivity of said mounting medium, wherein the thermal conductivity is determined based on the weight ratio between the granular resin and the granular filler.

15. The method according to claim 14, wherein said method is part of a series production of sample preparations and wherein a cycle time of each production is determined by controlling heat conductivity of the mounting medium.

16. The method according to claim 15, wherein said heat conductivity is controlled by blending said granular resin with granular metal filler having heat conductivity which is higher than the heat conductivity of said granular resin.

17. The method according to claim 9, wherein said method forms part of a preparation process for materialographic and/or metallographic analysis.

18. The method according to claim 9, wherein said moulding cavity is a compression moulding cavity.

19. The method according to claim 9, wherein said first period of time and/or said second period of time, is reduced by increasing the weight ratio of said granular filler in said mounting medium.

20. A method of preparing a chemically non-reactive granular mounting medium for a sample material wherein said granular mounting medium is configured for fixating said sample material by means of a sintering process in a compression mould, comprising:

blending a thermoplastic granular resin and a granular metal filler to a weight ratio between the granular resin and said granular metal filler of 20-40% granular resin and 60-80% granular metal filler, alternatively, 28-32% granular resin and 68-72% granular metal filler, alternatively 30% granular resin and 70% granular metal filler.

21. The method according to claim 20, wherein the metal filler is aluminium.

* * * * *